United States Patent [19]

Termin

[11] Patent Number: 5,374,397
[45] Date of Patent: Dec. 20, 1994

[54] DEVICE FOR MEASUREMENT OF NO CONTENTS

[76] Inventor: Andreas P. Termin, 400 Raymondale Dr. #11, South Pasadena, Calif. 91030

[21] Appl. No.: 144,198

[22] Filed: Oct. 27, 1993

[30] Foreign Application Priority Data

Nov. 2, 1992 [DE] Germany .............. 4236944

[51] Int. Cl.$^5$ .............. G01N 21/76; G01N 33/50
[52] U.S. Cl. ................ 422/80; 422/68.1; 422/81; 422/82.08; 436/116
[58] Field of Search ........... 422/68.1, 80, 81, 82.05, 422/82.08; 436/106, 107, 108, 116–118

[56] References Cited

U.S. PATENT DOCUMENTS 4,221,761 9/1980 Bullens et al. .............. 422/54

FOREIGN PATENT DOCUMENTS

249912A2 6/1987 European Pat. Off. ...... G01N 2/76
2225696A1 12/1972 Germany ................. G01N 21/52

OTHER PUBLICATIONS

Peter Mordvintcev, et al., On Line Detection of Nitric Oxide Formation in Liquid Aqueous Phase by Electron Paramagnetic Resonance Spectroscopy, 1991, pp. 142–146.

Mark Bollinger and Robert E. Sievers, Conversion of Nitrogen Dioxide, Nitric Acid, and n-Propyl Nitrate to Nitric Oxide by Gold-Catalyzed Reduction with Carbon Monoxide, 1983, pp. 1980–1986.

Oliver C. Zafiriou and Mack McFarland, Determination of Trace Levels of Nitric Oxide in Aqueous Solution, 1980, pp. 1662–1667.

Chemical Abstracts, vol. 113, (16), 1990, Ref.: 139557g.

Primary Examiner—James C. Housel
Assistant Examiner—David Redding
Attorney, Agent, or Firm—Blakely, Sokoloff Taylor, Zafman

[57] ABSTRACT

The present invention relates to a device for the measurement of NO contents in liquids using an inert carrier gas, where the device consists out of micro reaction part FIG. 1 which is divided into an inert gas inlet nozzle 1, the microreaction vessel 2 with frit 3, at least one inlet nozzle for the injection of the liquid to be analyzed 4, as well as a cooled outlet nozzle for the inert gas loaded with NO 5, and a detector 6, with which the NO content of the inlet liquid is measured and evaluated, and where the $NO_2^-$ ions present in the solution are reduced back to NO using a reaction mixture consisting out of 1,1'dimethylferrocene in acetonitrile in an acidic medium, preferably perchloric acid.

2 Claims, 3 Drawing Sheets

DEVICE FOR MEASUREMENT OF NO CONTENTS

STATEMENT AS TO THE RIGHT OF INVENTION

The invention is made by a single inventor employed by the CALIFORNIA INSTITUTE OF TECHNOLOGY.

BACKGROUND OF THE INVENTION

1. Field of the Invention

Nitric oxide is a short lived radical and has recently been found to be produced by various mammalian cells e.g., endothelial cells, macrophages and nerve cells. It influences the blood pressure, is a neurotransmitter and a tool of the immune response.

The detection and evaluation of the nitric oxide (NO) can be performed in different ways.

2. Related Art

The state of art shows different methods for detecting nitric oxide, for example as a color complex using sulfanile acid (Bell, F. K., O'Neill, J. J., Burgison, R. M., *J. Pharm. Sci.*, 1963, 52, 637-639) (diazotation with NO and coupling with N (1-naphthyldiamine)), or with oxyhemoglobin (Doyle, M. P., Hoekstra, J. W., *J. Inorg. Biochem.*, 1981, 14, 351-358), ESR-spectroscopic (Wennhalm, A., Peterson, A-S., *J. Cardiovasc. Pharmacol.*, 1991, 17/3, S34-S40), mass-spectroscopic (Palmer, R. M. J., Ashton, D. S., Moncada, S., *Nature*, 1988, 333, 664-666), with the help of spin-traps (Korth, H-G., Ingold, K. U., Sustmann, R., Groot, deH., Sies H., *Angew. Chem. Int. Ed. Engl.*, 1992, 31/7, 891-893), electrochemical (Shibuki, K., *Neuroscience Research*, 1990, 9, 69-76; Taha, Z., Malinski, T., *Nature*, 1992, 358, 676-678) or using chemiluminescence (Downes, M. J., Edwards, M. W., Elsey, T. S., Walters, C. L., *Analyst*, 1976, 101, 742-748)

The chemiluminescence method used in the present inventive method relates to the reaction of NO and ozone to $NO_2^*$ and $O_2$. During the subsequent decay of $NO_2^*$ light of the wavelength 600-875 nm is emitted, which can be measured using a photodetector.

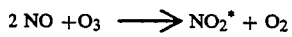
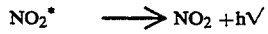

Nitric oxide is a very reactive gas, that can be easily oxidized to $NO_2^*$ (nitrite) in the presence of oxygen. For evaluating the exact amount of NO in liquids it is necessary to reduce the nitrite formed as an intermediate back to NO.

According to the current state of the art (Cox, R. D., *Anal. Chem.*, 1980, 52, 332-335), a reaction vessel with refluxing acidic acid containing 1% sodium iodide (NaI) is used and NO/water solutions are used as standards.

The sample is introduced into the reducing medium which is purged with helium for approximately 60 sec. A valve of the NO-detector is opened and the NO is transferred into the NO detector. An alkaline cooling trap prevents that the acidic vapors contaminate the NO-detector.

This system displays the following disadvantages:

a) the reaction vessel has to be heated,
b) the temperature of the reaction vessel has to be held precisely to prevent fluctuations of the ground signal,
c) the hot acidic vapors have to be cooled down and afterwards the gas stream has to be fed through an alkaline cooling trap, which leads to a considerable expansion of the total volume of the device followed by a reduction of the NO concentration in the gas stream, and therefore to measurement inaccuracies.
d) work intensive standard curves have to be done
e) the reduction is considerably slow {~1 minute} (Hoffman, M. R., Menon, N. K., Bing, R. J., *J. of Applied Cardiology*, 1990, 5, 455-460).

SUMMARY OF THE INVENTION

The task of the present invention was to find particularly mild reducing conditions, which is important for analyzing physiological liquids, like for example effluents from cell preparations. Physiological liquids contain various organic compounds that will be also reduced, if the conditions are tool harsh. Furthermore, there are limitations to overcome due to the limited amount of reduction medium in a micro reaction vessel.

Therefore, the inventive task was to eliminate all of the above described insufficiencies by simplifying the procedure. It should be carried out at room temperature leading to a reduction in measurement fluctuations, and to achieve a high sensibility of the method by reducing the total volume of the device. Furthermore, continuous sampling should be possible.

This task was resolved by a method for the reduction of $NO_2^-$ to nitric oxide in liquids containing nitric oxide, wherein said, that the reaction runs in the apparatus according to FIG. 1 using an inert carrier gas. The micro reaction part FIG. 1 is subdivided into the inert gas inlet nozzle 1, the micro reaction vessel 2 with frit 3, at least one inlet nozzle for the liquid to be analyzed 4, a cooled outlet nozzle for the inert gas loaded with NO 5, and a detector for measuring and evaluating the NO-content of the liquid. The reaction can be carried out at a temperature range of 5° C.-50° C. The reaction medium consists of 1,1'dimethylferrocene in acetonitrile under acidic conditions. The mixing of the reaction medium is achieved by an inert gas stream that is fed into the reaction medium through a frit and the inert gas is used simultaneously as carrier gas for the nitric oxide, which is carried out via outlet nozzle 5 to the detector 6 where the total NO content is analyzed. Preferably, 70% perchloric acid is used as acidic medium and room temperature is the chosen reaction temperature. The reduction is exothermic and extremely fast (Fukuzumi, S., Yorisue, T., *Chemistry Lett.*, 1990, 871-874).

Due to the low reaction temperature and the relatively high boiling point of the reaction media and to the very low flow of the inert carrier gas through the reaction medium, the rise in vapor partial pressure is that small that it can be neglected.

These circumstances proved to be an advantage for the total concept, method and device, because undesired brine particles do not reach the detection part of the apparatus FIG. 2.

Furthermore, cooling devices that increase the total volume are not necessary.

Therefore, the outlet nozzle 5 is only designed as a pipe surrounded by a cooling mantle 7, cooled by constant water flow (~10° C.).

Inert gases used are noble gases, preferably helium.

A further advantages development of the new method for analyzing physiological effluents of cell preparations is that the liquid to be analyzed for its NO content is directly injected into the reaction medium in vessel 2 via inlet nozzle 4 through the septum 8 in FIG. 1. This reduces measurement fluctuations due to possible spilling of the liquid sample at the glass parts of the device. A stable sodium nitrite solution is used as standard control.

The 1,1'dimethylferrocene/acetonitrile/perchloric acid mixture with a perchloric acid concentration of preferably 1% used in the new inventive method also displays the advantage that it can be hardly affected by dilution. Therefore, continuous sampling into the same reducing solution is possible. FIG. 3 shows measurements in which 500 pmol sodium nitrite diluted in 100 µl water are added each time to the 2,15 ml reduction medium. The signal displayed in mV stays almost the same.

DESCRIPTION OF THE DRAWINGS

The following descriptions and examples describe the invention in detail.

The micro reaction part FIG. 1 is subdivided into the inert gas inlet nozzle 1, the micro reaction vessel 2 with frit 3, at least one inlet nozzle for the liquid to be analyzed 4, an outlet nozzle for the inert gas loaded with NO 5 surrounded by a cooling mantle 7. The samples are injected through the septum 8. The gas flow of the evacuation of the micro reaction vessel are controlled by vacuum tight Teflon valves 16, 17. Total volume of the apparatus from the frit 3 to the teflon stopcock 17 is 35 ml; inner diameter of the inlet and outlet nozzle is 4 mm; inner diameter of the microreaction vessel 2 is 20 mm.

Figure 1:
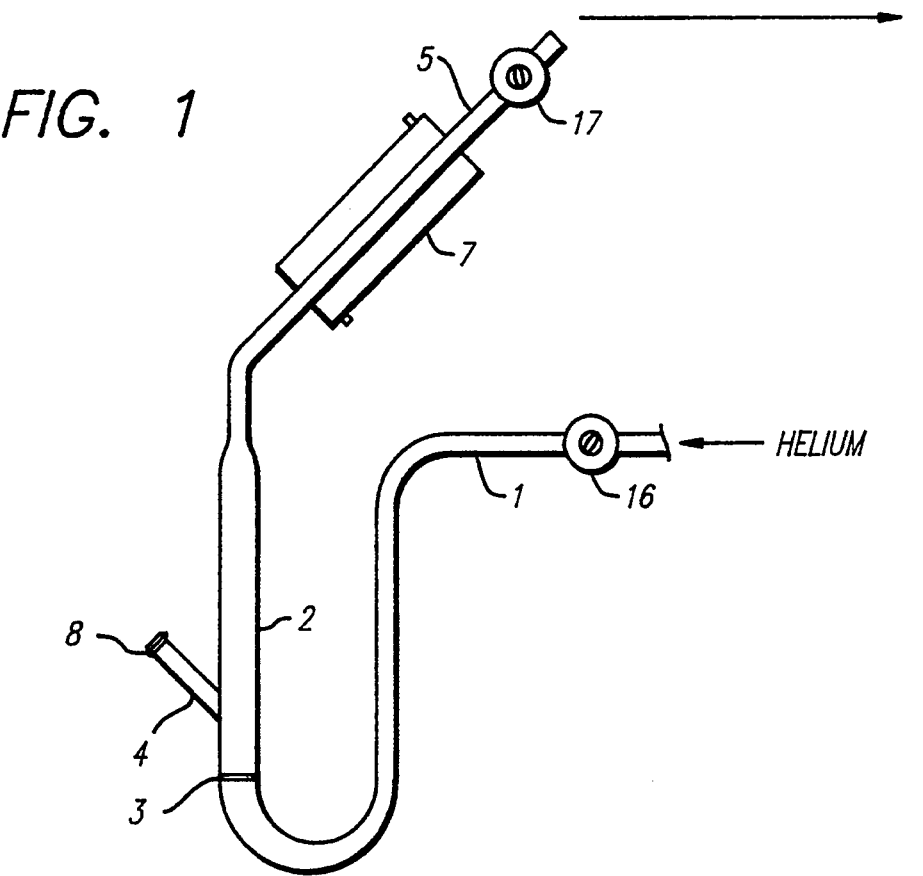
FIG. 1 shows a device for the reduction of NO/-$NO_2^-$-containing solutions. The total NO content is set free and carried to the detector and recorder unit FIG. 2, where the total NO content is evaluated.
Figure 2:
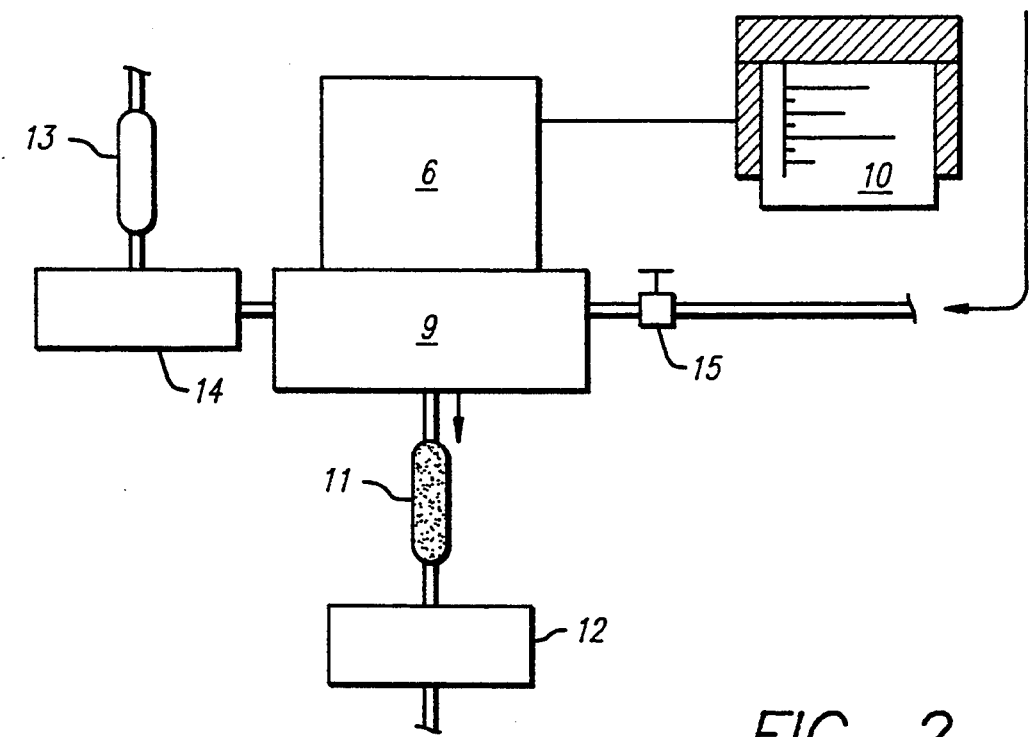
FIG. 2. shows the NO detector and recorder.
Figure 3:
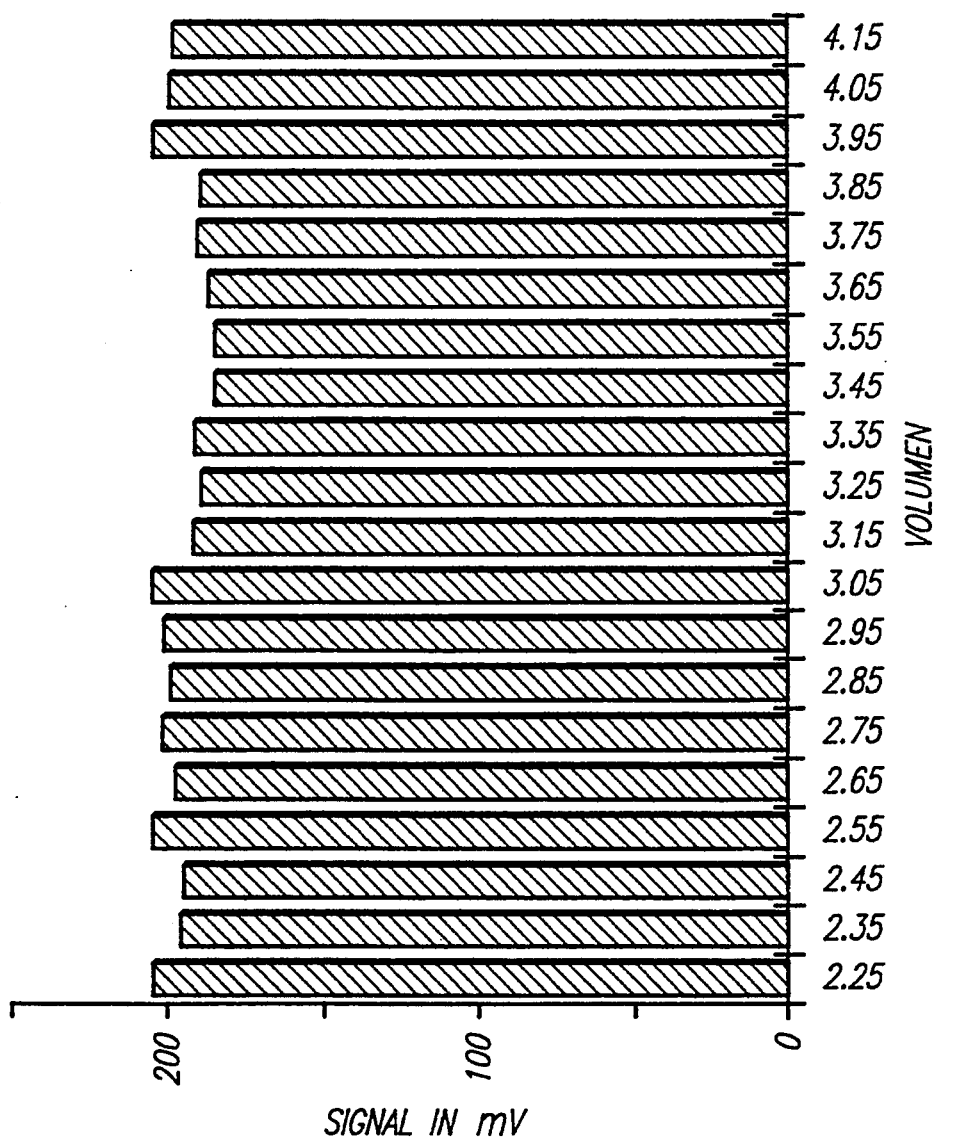
FIG. 3. 500 µmol sodium nitrite diluted in 100 µl water is added each time to 2.15 ml of the reducing solution; the signal indicated by mV is almost not affected by the dilution.

After leaving the microreaction part FIG. 1 the inert gas stream carries the ntiric oxide to the NO-analyzer, where the NO-detector 6 measures the emitted light in the chemiluminescence generator 9 the data are recorded 10. The NO-analyzer is equipped with a active charcoal filter 11 (to destroy residues of ozone), a vacuum pump 12 to maintain a proper vacuum in the reaction chamber and an oxygen supply 13 for the ozone generator 14. The valve 15 regulates the flow of the carrier gas into the chemiluminescence generator 9.

PREFERRED EMBODIMENT

The inventive method and device is used for the determination of NO release by mammalian cells. Bovine endothelial cells, for example, are detached from the inner wall of bovine aortas using collagenase and transferred to microcarrier beads. The cell density is defined and a cell aliquot (120 billion cells) are transferred onto a filter, 105 µm pore diameter and superfused with Krebs-Henseleit solution at a known rate with a temperature of 37° C. The filtrate is then injected into the device of FIG. 1 for the determination of its NO content.

The NO determination is carried out under normal conditions. No preventive measures are taken with regard to the oxidation of the NO to $NO_2^-$. In order to determine the total nitrogen oxide content the meanwhile formed $NO_2^-$ has to be reduced to NO.

For this purpose a reduction solution consisting of 30 mg 1,1'dimethylferrocene solved in 3 ml HPLC grade acetonitrile acidified by 49 µl of perchloric acid (70%) has been prepared. 2 ml of this solution is introduced via inlet nozzle 4 into the device of FIG. 1. In advance, the inlet valve 16 has been opened and helium has been infused into the apparatus with a flow of 35 ml per minute. Simultaneously the outlet valve 17 and the regulation valve 15 have been opened. 200 µl of the above described fresh cell effluents are now injected using a gastight syringe through the injection septum 8 via inlet nozzle 4 directly into the reduction solution of the microreaction vessel 2. The sample contains the NO content produced by 120 billion freshly harvested endothelial cells.

The cooling water in the cooling mantle 7 has a temperature of 10° C.

NO leaves the vessel via outlet nozzle 5 carried by a helium stream into the chemiluminescence generator 9, where the emitted light displays a wavelength of 600–875 nm and is proportional to the NO concentration in the gas stream.

The NO concentration is indicated as pmol/ml.

Five different experiments lead to the following NO values expressed as pmol per analyzed filtrate.

| 1 | 232 pmol |
| 2 | 162 " |
| 3 | 874 " |
| 4 | 675 " |
| 5 | 426 " |

The following data of dimensions display the volume minimization of the device according to FIG. 1.

Figure 4:
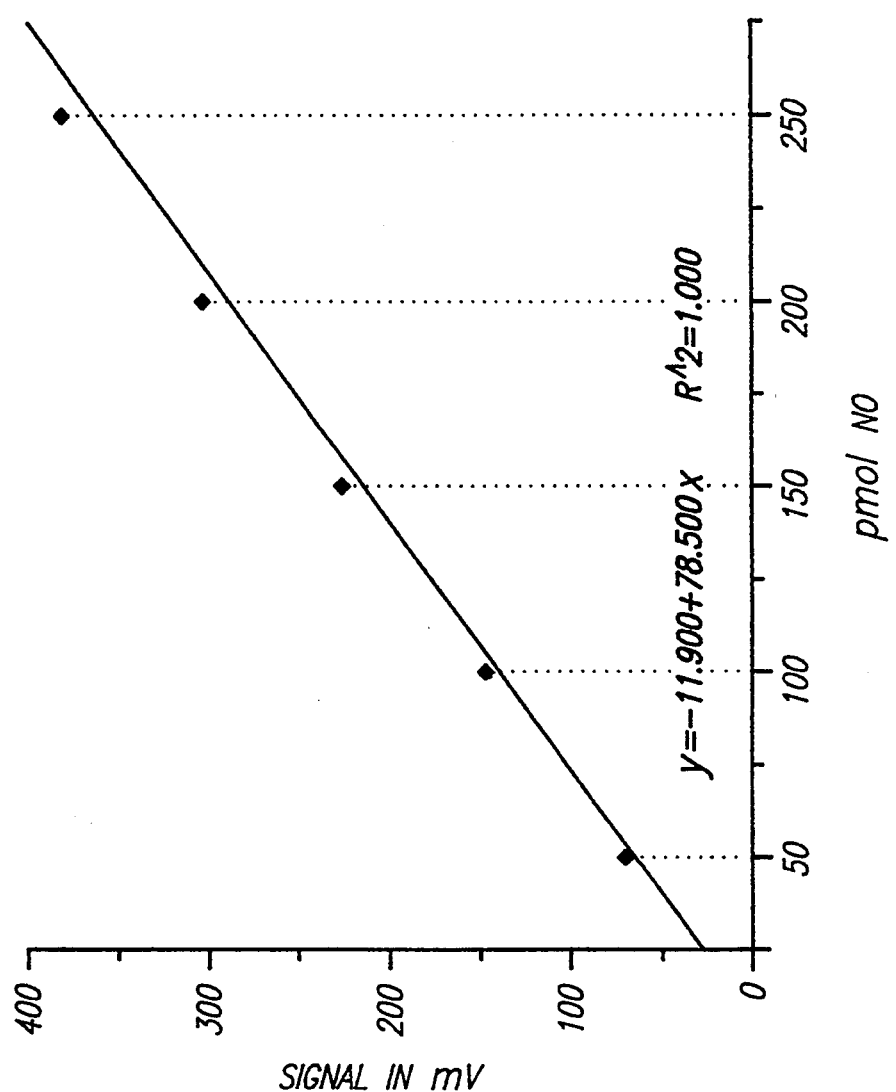
FIG. 4. standard curve of NO concentration versus detector signal in mV.

The NO standard curve is obtained by injecting small volumes of defined amounts of dissolved sodium nitrite, which is reduced to NO according to the inventive method, proves the high precision and reproducibility of the new method as displayed in FIG. 4.

What is claimed:

1. Device for the measurement of NO contents in liquids using an inert carrier gas, wherein said device comprises:
    a microreaction vessel with frit,
    a minimum of one inlet nozzle, attached to said reaction vessel, with an injection septum where the liquid to be analyzed can be injected,
    an inert gas inlet nozzle attached to a first end of said reaction vessel,
    an outlet nozzle attached to a second end of said reaction vessel for the inert gas loaded with NO to exit said reaction vessel a means for cooling said outlet nozzle and corresponding inert gas loaded with NO exiting said nozzle, and
    a detector to receive said inert gas loaded with NO after it exits said second end of the reaction vessel, which measures and determines the NO content of the analyzed liquid.

2. Device according to claim 1, wherein said inert gas inlet nozzle and outlet nozzle have valves comprising polytetrafluoroethylene or are covered by such material that said microreaction vessel has an internal volume up to a maximum of 20 ml and said vessel, said minimum of one inlet nozzle with injection septum, said inlet nozzle and said outlet nozzle, are constructed of glass.

* * * * *